US006427532B1

(12) United States Patent
Keller

(10) Patent No.: US 6,427,532 B1
(45) Date of Patent: Aug. 6, 2002

(54) DEVICE FOR MEASURING A FILL LEVEL OF A LIQUID IN A CONTAINER

(75) Inventor: Dieter Keller, Aschaffenburg (DE)

(73) Assignee: Mannesmann VDO AG, Frankfurt am Main (DE)

( * ) Notice: Subject to any disclaimer, the term of this patent is extended or adjusted under 35 U.S.C. 154(b) by 71 days.

(21) Appl. No.: 09/654,618

(22) Filed: Sep. 5, 2000

(30) Foreign Application Priority Data

Sep. 4, 1999 (DE) .......................................... 199 42 379

(51) Int. Cl.[7] .............................................. G01F 23/00
(52) U.S. Cl. ...................... 73/290 V; 73/570; 181/124; 324/323; 367/87; 367/95; 367/97
(58) Field of Search .............................. 73/290 V, 540; 324/323; 181/124; 367/87, 95, 97

(56) References Cited

U.S. PATENT DOCUMENTS

| | | | | |
|---|---|---|---|---|
| 4,470,299 A | * | 9/1984 | Soltz | 73/290 V |
| 4,531,406 A | | 7/1985 | Fritz | |
| 4,770,038 A | * | 9/1988 | Zuckerwar et al. | 73/290 V |
| 5,119,676 A | | 6/1992 | Bower et al. | 73/290 |
| 5,226,320 A | * | 7/1993 | Dages et al. | 73/290 V |
| 5,586,085 A | * | 12/1996 | Lichte | 367/99 |
| 5,793,705 A | * | 8/1998 | Gazis et al. | 367/98 |
| 5,799,534 A | * | 9/1998 | Van der Pol | 73/290 V |
| 5,827,943 A | * | 10/1998 | Schmidt | 73/1.73 |
| 5,877,997 A | * | 3/1999 | Fell | 367/99 |

FOREIGN PATENT DOCUMENTS

| | | | | |
|---|---|---|---|---|
| DE | 37 06 453 | 9/1988 | | G01F/23/28 |
| DE | 43 28 046 | 3/1994 | | G01F/23/28 |
| DE | 196 00 097 | 7/1997 | | G01F/23/296 |
| EP | 0 138 541 | 10/1984 | | G01F/23/28 |
| FR | 1219895 | 5/1960 | | |
| WO | WO 91/02950 | 8/1990 | | G01F/23/28 |
| WO | WO 98/04889 | 7/1996 | | G01F/23/296 |

* cited by examiner

Primary Examiner—Hezron Williams
Assistant Examiner—Katina Wilson
(74) Attorney, Agent, or Firm—Cohen, Pontani, Lieberman & Pavane

(57) ABSTRACT

A device for measuring a fill level of a liquid includes an ultrasonic sensor with two sensor elements. One of the sensor elements determines the echo time of an ultrasonic wave to a float which follows the liquid level. The other of the sensor elements determines the echo time of the ultrasonic wave up to a measuring reflector arranged at a known distance from the other of the sensor elements. An evaluation unit compares the echo times and determines the fill level of the liquid from the ratio of echo times and from the known distance to the measuring reflector.

7 Claims, 2 Drawing Sheets

DEVICE FOR MEASURING A FILL LEVEL OF A LIQUID IN A CONTAINER

BACKGROUND OF THE INVENTION

1. Field of the Invention

The invention relates to a device for measuring a fill level of a liquid in a container, more specifically a fuel tank of a motor vehicle, the device having an ultrasonic sensor for generating ultrasonic waves in the liquid and for receiving the ultrasonic waves reflected in the region of the liquid level in the container and an evaluation unit for calculating the fill level of the liquid from the echo time of the ultrasonic waves received by the ultrasonic sensor.

2. Description of the Related Art

A device for measuring the fill level of fuel in a fuel tank using an ultrasonic sensor is known in which the ultrasonic sensor has an outside diameter corresponding to the inside diameter of a measuring tube arranged in the fuel tank. The ultrasonic sensor is plugged into an end of the measuring tube. The measuring tube penetrates the bottom of the container and is filled with the liquid present in the fuel tank via compensating bores. To amplify the ultrasonic waves reflected by the liquid level, a float for reflecting the ultrasonic waves is arranged in the measuring tube.

A disadvantage of the known device is that the echo time of the reflected ultrasonic waves depends very strongly on the composition of the liquid and on its temperature. The device provided for use in the fuel tank of a motor vehicle, in particular, is very inaccurate because the temperature of the fuel varies over a large range such as, for example, upon refilling or upon parking in the sun.

One solution is to measure the temperature in the tank and to correct the echo time of the ultrasonic waves in accordance with the temperature and material characteristics of the liquid. However, this requires a complex calculation of the fill level. Moreover, in the case, for example, of diesel fuel it is not possible to correct a change in the composition of diesel fuel which occurs as better fuels are developed or a change in composition associated with water absorption.

SUMMARY OF THE INVENTION

The object according to the present invention is to provide a device for detecting the fill level of liquid in a container via reflections of an ultrasonic wave detected by a sensor, wherein the sensor provides a reliable detection for liquids of varying temperature and composition.

The object according to the present invention is met by a measuring reflector arranged in a bottom region of the container and at a designated spacing upstream of the ultrasonic sensor and an evaluation unit operating arranged for comparing the echo times of the ultrasonic waves reflected in the region of the liquid level and of the ultrasonic waves reflected by the measuring reflector.

This configuration allows a change in the echo time of the ultrasonic waves reflected in the region of the liquid level through temperature variations or variations in the composition of the liquid to be easily accounted for by comparison with the echo time of the ultrasonic waves reflected by the measuring reflector. The fill level of the liquid in the container may be specified., for example, as a function to a ratio of the echo times and the spacing of the ultrasonic sensor from the measuring reflector. Since the ratio of echo times is independent of the composition of the liquid and its temperature in the container, the fill level is determined particularly accurately. A further advantage of this configuration is that a single device may be produced and mounted without calibration for any desired liquid. This reduces production costs of the device, particularly when the device comprises fuel tanks of motor vehicles and large numbers of the devices are mass produced.

A particularly accurate fill level may be determined using the device according to the invention when the measuring reflector is moveable from a lateral position at the designated spacing upstream of the ultrasonic sensor. The determination of the echo time of the reflection from the measuring reflector and of the echo time of the reflections from the liquid level is thereby performed sequentially. Therefore, the reflections do not mutually influence or interfere with one another.

The device having a movable reflector may comprise a simple design such as, for example, a slide which can be moved into the designated position or a flap. The movement of the slide or the flap may be effected mechanically, electrically, hydraulically, pneumatically, or magnetically.

The device according to another embodiment of the present invention requires no moving parts when the ultrasonic sensor comprises two sensor elements in which one of the sensor elements is arranged for determining the echo time of the reflections of the measuring reflector and the other of the two sensor elements is arranged for determining the echo time of the reflections from the liquid level. This arrangement of the two sensor elements also prevents mutual influencing of the reflections.

The device according to the present invention may be cost-effectively produced when the measuring reflector is arranged on a splash pot bearing against the bottom of the container. Since the splash pot is located at the deepest point of the container, it is easy to ensure that a sufficient amount of liquid is always present on the section between the ultrasonic sensor and measuring reflector.

In accordance with another advantageous embodiment of the present invention, disturbing reflections may easily be avoided when the ultrasonic sensor is fastened on the outside of the container and is arranged opposite a measuring tube arranged in the container. The measuring tube can thereby be guided from the lower up to the upper wall of the container. The measuring tube may also bear the measuring reflector.

The device according to the present invention requires minimal components for mounting when the measuring tube comprises a stepped design with the measuring reflector arranged on the lowermost step. In this embodiment, a single ultrasonic sensor receives the two reflections of the measuring reflector and the liquid level. Separation of the signals is then performed in the evaluation unit.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings, wherein like reference characters denote similar elements throughout the several views.

DETAILED DESCRIPTION OF THE PRESENTLY PREFERRED EMBODIMENTS

Figure 1:
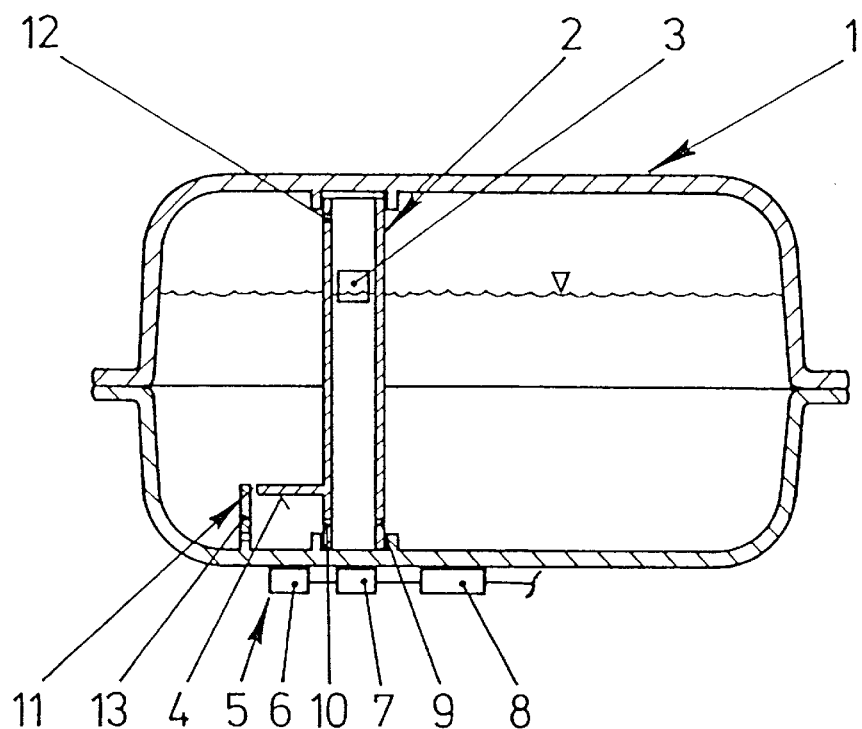
FIG. 1 is a longitudinal sectional view of a container including a device for measuring a fill level according to the present invention.

FIG. 1 shows a container 1 constructed as a fuel tank for a motor vehicle with a measuring tube 2 arranged therein. A float 3 is arranged in the measuring tube 2 so that the float 3 follows the liquid level in the measuring tube 2 and is guided by the sides of the measuring tube 2. A laterally projecting measuring reflector 4 is arranged on a side of the measuring tube 2. An ultrasonic sensor 5 with two sensor elements 6, 7 and an evaluation unit 8 are arranged on the outside of the tank 1. One of the sensor elements 7 is arranged below the measuring tube 2 while the other sensor element 6 is arranged below the measuring reflector 4. The sensor elements 6, 7 each transmit an ultrasound signal vertically upward and receive the reflection. The ultrasonic signal of the sensor element 7 is reflected by the float 3 and the ultrasound signal produced by the other sensor element 6 is reflected by the measuring reflector 4. The evaluation unit 8 measures the echo time, i.e., the time between transmission of the ultrasonic signal and reception of the reflection for each ultrasonic signal, and determines the fill level of the fuel in the container 1 from the ratio of the echo times and from the known location of the measuring reflector 4. The fill level may then be converted to the volume of the fuel given a known tank geometry. The fuel penetrates into the measuring tube 2 and into the region upstream of the measuring reflector 4 via compensating openings 9, 10, 11, 12 arranged in the measuring tube 2 and next to the measuring reflector 4. The container 1 also includes a wall 13 standing vertically upward adjacent a free end of the measuring reflector 4. This wall 13 screens the ultrasonic sensor 5 from lateral reflections.

Figure 2:
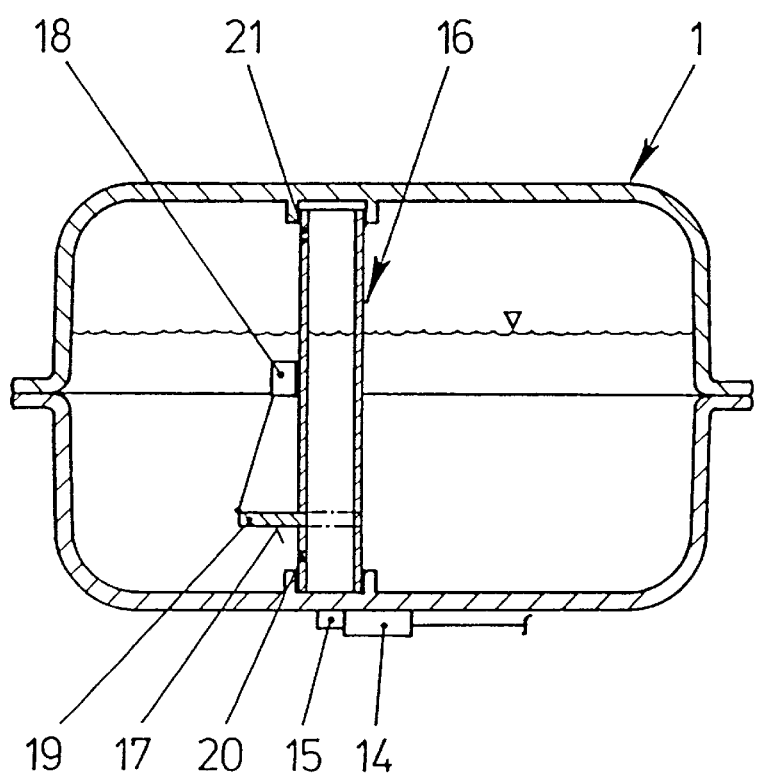
FIG. 2 is a longitudinal sectional view showing a further embodiment of the device for measuring a fill level with a movable measuring reflector.

FIG. 2 shows a further embodiment of the device according to the present invention with an evaluation unit 14 and an ultrasonic sensor 15 which together form a structural unit. The ultrasonic sensor 15 is arranged opposite a measuring tube 16 with a movable measuring reflector 17. The measuring reflector 17 has a slide 19 which can be moved by an actuator element 18. The slide 19 may be moved by the actuator element 18 for shifting the measuring reflector 17 from an outer position drawn on the outside of the measuring tube 16 in FIG. 2 into an inner position illustrated by dashed and dotted lines in FIG. 2 inside the measuring tube 16. By appropriately driving the actuator element 18, the echo time of the ultrasonic waves to the liquid level or to the measuring reflector 17 may be selectively determined. By contrast with the embodiment according to FIG. 1, the ultrasonic signal is reflected here directly from the liquid level without a float. Of course, a float may also be used in this embodiment to amplify the reflection. Near its upper and lower ends, the measuring tube 16 respectively has compensating openings 20, 21 for pressure equalization and material balancing with the remaining part of the container 1.

Figure 3:
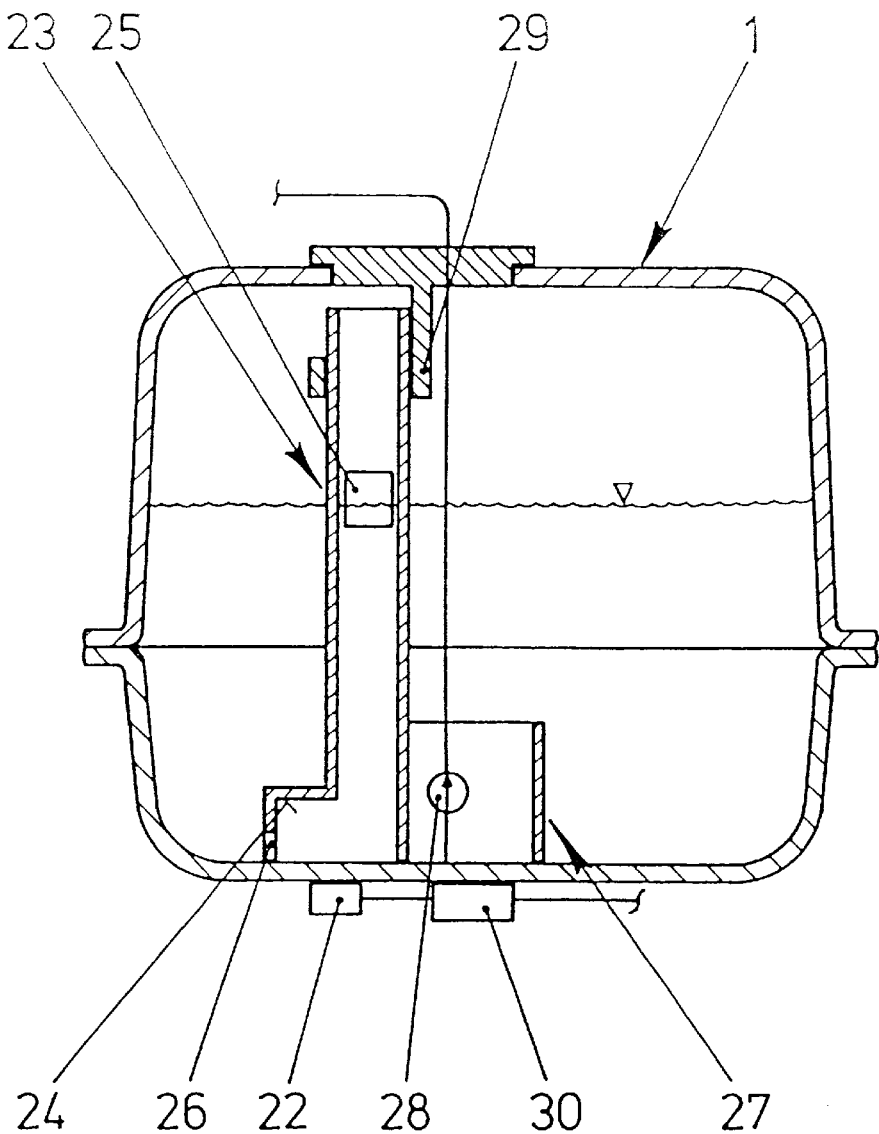
FIG. 3 is a longitudinal sectional view of a device according to the present invention with a measuring reflector arranged in a measuring tube.

FIG. 3 shows a further embodiment of the device according to the present invention with an ultrasonic sensor 22 arranged below a stepped measuring tube 23. A measuring reflector 24 is arranged on the lower step of the measuring tube 23 and a float 25 for amplifying reflections is axially displaceably guided in a remaining part of the measuring tube 23. The upper end of the measuring tube 23 is open and a compensating opening 26 is arranged in a lower region of the measuring tube. As a result, the liquid flows freely into the measuring tube from the container 1 so that the fill level of the measuring tube and the container is equalized. The float 25 thereby follows the fill level of the liquid in the container 1. The measuring tube 23 is produced in one structural piece with a splash pot 27 of a delivery pump 28 and is prestressed by a holder 29 against the bottom of the tank 1. Ultrasound signals transmitted by the ultrasonic sensor 22 are reflected both by the measuring reflector 24 and by the float 25. The evaluation unit 30 evaluates the two reflections independently of one another. The reflection of the measuring reflector 24 may be differentiated by the echo time, which is shorter than the other reflection. Alternatively, a plausibility test in the case of approximately known material characteristics and temperatures of the liquid may be used to determined which reflected signal is the reflection of the measuring reflector 24.

While there have been shown and described and pointed out fundamental novel features of the present invention as applied to a preferred embodiment thereof, it will be understood that various omissions and substitutions and changes in the methods described and in the form and details of the devices illustrated, and in their operation, may be made by those skilled in the art without departing from the spirit of the present invention. For example, it is expressly intended that all combinations of those elements which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

I claim:

1. A device for measuring a fill level of a liquid in a container, comprising:

an ultrasonic sensor operatively arranged for generating an ultrasonic signal in the liquid and for receiving a first reflection of the ultrasonic signal reflected in the region of the fill level of the liquid in the container;

a measuring reflector arranged in a bottom of the container at a spacing upstream of said ultrasonic sensor, wherein said ultrasonic sensor receives a second reflection of the ultrasonic signal reflected from the measuring reflector; and an evaluation unit operatively connected to said ultrasonic sensor for determining the fill level of the liquid in the container by comparing a first echo time comprising the time between generating the ultrasonic signal and receiving the first reflection and a second echo time comprising the time between generating the ultrasonic signal and receiving the second reflection.

2. The device of claim 1, wherein said measuring reflector is selectively moveable away from a lateral position at the spacing upstream of said ultrasonic sensor.

3. The device of claim 2, wherein said measuring reflector comprises one of a slide and a flap that is selectively movable into the lateral position.

4. The device of claim 1, wherein said ultrasonic sensor comprises first and second sensor elements, wherein said first sensor element is operatively arranged for determining said first echo time and said second sensor element is operatively arranged for determining said second echo time.

5. The device of claim 1, further comprising a splash pot bearing against a bottom of said container, wherein said measuring reflector is arranged on said splash pot.

6. The device claim 1, further comprising a measuring tube arranged in said container, wherein said ultrasonic sensor is fastened on an outside of the container and arranged opposite an end of said measuring tube.

7. The device of claim 6, wherein said measuring tube comprises a stepped measuring tube having a lowermost step and said measuring reflector is arranged on said lowermost step.

* * * * *